(12) United States Patent
Bernard et al.

(10) Patent No.: US 7,115,770 B2
(45) Date of Patent: Oct. 3, 2006

(54) USE OF TIN DERIVATIVES AS CATALYSTS

(75) Inventors: Jean-Marie Bernard, Mornant (FR); Bernard Jousseaume, Talence (FR); Christian Laporte, Castanet-Tolosan (FR); Thierry Toupance, Talence (FR)

(73) Assignee: Rhodia-Chimie, Aubervilliers (FR)

( * ) Notice: Subject to any disclaimer, the term of this patent is extended or adjusted under 35 U.S.C. 154(b) by 515 days.

(21) Appl. No.: 10/398,837

(22) PCT Filed: Oct. 8, 2001

(86) PCT No.: PCT/FR01/03093

§ 371 (c)(1), (2), (4) Date: Apr. 9, 2003

(87) PCT Pub. No.: WO02/30565

PCT Pub. Date: Apr. 18, 2002

(65) Prior Publication Data

US 2004/0087812 A1    May 6, 2004

(30) Foreign Application Priority Data

Oct. 13, 2000  (FR)  .................................. 00 13164

(51) Int. Cl.
*B01J 31/02* (2006.01)
*C07C 269/00* (2006.01)

(52) U.S. Cl. ...................... 560/157; 502/150; 502/152; 502/171; 502/174; 502/216; 502/224; 502/227; 502/200; 252/182.12

(58) Field of Classification Search ................ 560/157; 502/150, 152, 171, 174, 216, 224, 227, 200; 252/182.12
See application file for complete search history.

(56) References Cited

U.S. PATENT DOCUMENTS

| 4,268,683 | A | * | 5/1981 | Gurgiolo ..................... 560/24 |
| 6,010,976 | A | | 1/2000 | Ryu ........................... 502/156 |
| 6,133,473 | A | * | 10/2000 | Berrier ....................... 560/157 |
| 6,998,364 | B1 | * | 2/2006 | Bernard et al. ............. 502/150 |

FOREIGN PATENT DOCUMENTS

| DE | 43 17 428 | 6/1994 |
| DE | 197 56 748 | 7/1999 |

* cited by examiner

Primary Examiner—Stanley S. Silverman
Assistant Examiner—Timothy C. Vanoy

(57) ABSTRACT

The invention concerns the use as catalyst for transforming carbamates of compounds corresponding to the general formula (I): —Sn (X) (X') wherein: X' is selected among chloride, bromide, iodide, thiocyanate radicals, sulphonate radicals, advantageously perfluorinated on the carbon bearing the sulphonate function; X is selected among the values of X' and among radicals of formula Y-Z; Y is selected among the chalcogen groups, advantageously light (that is oxygen and sulphur); Z is selected in the group consisting of trisubstituted tin, monosubstituted zinc, and the oxygenated acid radicals after ignoring the OH function. The invention is applicable to the coating industry.

17 Claims, No Drawings

USE OF TIN DERIVATIVES AS CATALYSTS

This application is an application under 35 U.S.C. Section 371 of International Application Number PCT/FR01/03093 filed on Oct. 08, 2001.

A subject matter of the present invention is novel transcarbamation catalysts. The invention relates more specifically to the use of novel tin-based catalysts.

Because of their high reactivity and their relative toxicity, isocyanates are often used in a derived form or in a masked form. This derived form or this masked form exhibits the disadvantage corresponding to its advantages, that is to say that it is not very reactive, and consequently requires the use of catalysts in order for the reaction to be able to take place at temperatures acceptable in industry.

Masked isocyanates can be used in all the applications of isocyanates, namely paints, varnishes and more generally coatings, adhesives, and some specialty polymers.

The most widely used catalysts are dialkyltin alkanoates, the most well known of which is dibutyltin dilaurate. However, for some applications, dibutyltin dilaurate exhibits an insufficient activity and consequently it is necessary to use it at very high concentrations.

These transcarbamation catalysts make it possible to prepare polyurethanes, in particular aliphatic polyurethanes.

This is why one of the aims of the present invention is to provide a transcarbamation catalyst which is more active than dibutyltin dilaurate.

Another aim of the present invention is to provide a catalyst of the preceding type which can also be used for the carbamation of oximes.

Another aim of the present invention is to provide a transcarbamation catalyst which can be used to convert carbamates of methanol and carbamates of primary alcohols.

These aims, and others which will become apparent subsequently, are achieved by means of the use as transcarbamation catalysts of compounds of following general formula (I):

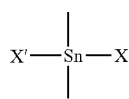

(I)

where:
X' is chosen from chloride, bromide, iodide or thiocyanate radicals or sulfonate radicals, advantageously perfluorinated on the carbon carrying the sulfonate functional group;
X is chosen from the values of X' and from radicals of formula Y-Z;
Y is chosen from the group of chalcogens, advantageously light chalcogens (that is to say, oxygen and sulfur);
Z is chosen from the group consisting of trisubstituted tin, monosubstituted zinc and residues of oxygen-comprising acids, the OH functional group not being included.

The compounds of this family exhibit a particularly advantageous catalytic activity. Among the compounds of the present family, the compounds where X' is a relatively heavy halide anion, that is to say chloride, bromide or iodide, should be more particularly indicated. The first two mentioned are preferred, in particular bromide. Relatively bulky anions, the associated acid of which exhibit a strong or very strong acidity, also give good results, in particular if they exhibit good solubility in fats. Mention may be made, among the acids giving anions which bring about good properties, of those which exhibit a $pK_a$ at most equal to 2. Mention may be made, among these acids, of sulfonic acids or stable carboxylic acids carrying an electron-withdrawing functional group on the carboxylic carbon, so that the $pK_a$ corresponds to the above restriction. Mention may in particular be made of perfluoroacetic acid.

Another acid which gives particularly satisfactory results is thiocyanic acid or more specifically its anion, thiocyanate. The preferred sulfonic acids are those for which the carbon carrying the sulfonic functional group carries at least two fluorine atoms.

Mention should be made, among the most active members of the family defined by the formula (I), of symmetrical compounds, that is to say those where X corresponds to the formula Y-Z and where Z and X'—Sn— are symmetrical, so that the chalcogen atom carries two identical radicals. In the formula (I), the "free" bonds of the tin are advantageously connected to hydrocarbonaceous groups, that is to say comprising hydrogen and carbon (but not necessarily comprising only hydrogen and carbon). These hydrocarbonaceous groups are advantageously chosen from aryls or alkyls (the latter being taken from alcohols, said alcohol functional group of which is not included); alkyls are preferred.

The combined radicals must be such that the carbon number of the compounds of formula (I) does not comprise at most 50 carbon atoms, preferably 25 carbon atoms.

The "free" bond of the zinc is generally connected to a hydrocarbonaceous compound, advantageously to the anion of an oxygen-comprising acid, advantageously a carboxylic acid.

These catalysts are advantageously used in an amount at least equal to 0.5% and at most equal to 5% as carbamate functional group equivalent, preferably between 1% and 2%.

The transcarbamation reaction depends on the alcohols and carbamates used. However, it is between 100 and 200° C., preferably between 120 and 180° C. The carbamates used are those resulting from the reaction of an isocyanate functional group with a hydroxyl functional group. Mention should be made, among hydroxyl functional groups, of alcohol functional groups, in particular those of alcohols which are volatile at the reaction temperature (boiling point at atmospheric pressure) and more particularly methanol.

Among the other hydroxyl functional groups which may be mentioned as exhibiting a specific advantage, phenol functional groups, hydroxyl functional groups grafted to a nitrogen atom, such as hydroxyimides, or oximes.

The alcohols which are substituted for these hydroxylated derivatives are advantageously polyols (especially di- and/or triols), advantageously primary polyols.

The molecular masses can vary within a wide range according to the form of the coating used. The molecular masses are relatively high, it being possible for them to range approximately up to 20 000 when the catalysts according to the present invention are employed in a powder paint, on the other hand, for more conventional applications, the polyols rarely exceed a molecular mass of approximately 3 000.

The molecular masses referred to are number-average molecular masses $M_n$ and are defined by the gel permeation technique known to "a person skilled in the art". More specifically, the molecular mass is determined by gel permeation chromatography (GPC). The technique uses two polystyrene gels (Ultrastyrogel® at $10^4$ and 500 Å) as gels, THF as solvent and sulfur as standards.

The isocyanates giving rise or corresponding to the carbamates which are preferred are at least partially aliphatic isocyanates, that is to say that the isocyanate functional group under consideration is connected via the nitrogen to the backbone of the isocyanate molecule by a carbon atom possessing $sp^3$ hybridization.

In addition, it is desirable, in the structure of the isocyanate [lacuna] or monomers (that is to say, isocyanates which are oligomerized subsequently, the commonest of which are hexamethylene diisocyanate and the compound denoted by the term isophorone diisocyanate, or IPDI), for the part of the backbone connecting two isocyanate functional groups to comprise at least one polymethylene sequence $(CH_2)_\pi$ where $\pi$ represents an integer from 2 to 10, advantageously from 4 to 8. This preference affects the mechanical performance. When there are several sequences, the latter can be alike or different. In addition, it is desirable, in a monomer, for these polymethylene sequences to be free to rotate and therefore exocyclic. When prepolymers, or oligomers, resulting from more than one monomer are used, it is desirable for the condition relating to this polymethylene sequence to be found in at least one of these monomers.

The preferred polyisocyanates are those which exhibit at least one aliphatic isocyanate functional group. In other words, at least one masked isocyanate functional group according to the invention is connected to the backbone via a carbon of $sp^3$ type advantageously carrying a hydrogen atom, preferably two. It is desirable for said carbon of $sp^3$ type to be itself carried by a carbon of $sp^3$ type advantageously provided with one and preferably two hydrogen atoms, this being in order to avoid the isocyanate group under consideration being in the neopentyl position. In other words, it is advisable to choose, as monomer (which monomers generally carry two isocyanate functional groups), at least one compound which carries at least one aliphatic [lacuna] functional group which is neither secondary nor tertiary, nor neopentyl.

In the case of a mixture obtained from several (in general two) types of monomers, it is preferable for that or those of the monomers which correspond to the above conditions and/or (advantageously "and") to the condition with regard to the presence of polymethylene sequence $(CH_2)_\pi$ to represent at least ⅓, advantageously ½, preferably ⅔, of the masked isocyanate functional groups. Thus, during the study according to the present invention, excellent results were obtained with mixtures comprising ⅔ of HMDT (hexamethylene diisocyanate "trimer") with IPDI or IPDT (IPDI "trimer"), the two being masked according to the invention (nBDI, norbornane diisocyanate, and its trimer are similar).

Of course, preference is given to the case where all the isocyanates are aliphatic and also correspond to the above criterion.

According to the present invention, the masked isocyanate, pure or as a mixture, results from a polyisocyanate, that is to say having at least two isocyanate functional groups, advantageously more than two (possibilities of fractional values since it generally relates to a mixture of more or less condensed oligomers), which itself generally results from a precondensation or from a prepolymerization of an individual diisocyanate (sometimes described as "monomer" in the present description).

The average molecular mass of these prepolymers or of these precondensates is generally at most equal to 2 000 (one significant figure), more commonly to 1 000 (one significant figure, preferably two).

Thus, among the polyisocyanates used for the invention, mention may be made of those of the biuret type and those for which the di- or trimerization reaction has resulted in four-, five- or six-membered rings. Among the six rings, mention may be made of the isocyanuric rings resulting from a homo- or hetero-trimerization of various diisocyanates alone, with other isocyanate(s) [mono-, di- or polyisocyanate(s)] or with carbon dioxide gas; in this case, a nitrogen of the isocyanuric ring is replaced by an oxygen. The oligomers comprising isocyanuric rings are preferred.

Mention should be made, among the most advantageous monomers, of, on the one hand, those which exhibit a polymethylene sequence as defined above which is exocyclic, obviously including noncyclic, among which may be mentioned tetramethylene diisocyanate optionally substituted by an alkyl group, advantageously of at most four carbon atoms, preferably of at most two carbon atoms; pentamethylene diisocyanate optionally substituted by an alkyl group, advantageously of at most four carbon atoms, preferably of at most two carbon atoms, and hexamethylene diisocyanate. Mention may be made, as monomers of cycloaliphatic nature which are preferably used in combination with isocyanates having exocyclic or noncyclic polymethylene sequences, of the monomers and the compounds resulting from the monomers below:

the compounds corresponding to the hydrogenation of the aromatic ring or rings carrying the isocyanate functional groups of aromatic isocyanate monomers, and in particular TDI (toluene diisocyanate) and biphenyl diisocyanates, the compound known under the abbreviation $H_{12}MDI$ and the various BICs [bis(isocyanatomethylcyclohexane)]; and especially norbornane diisocyanate, often known by its abbreviation NBDI;

isophorone diisocyanate or IPDI or 3-isocyanatomethyl-3,5-trimethylcyclohexyl isocyanate.

Another subject matter of the present invention is masked isocyanate compositions, the isocyanates being masked in the form of carbamates (lato sensu, that is to say the functional groups corresponding to the sequence —N(R)—CO—O— where R is a hydrocarbonaceous radical, generally an alkyl radical, indeed even an aryl radical, or more frequently a hydrogen), additionally comprising a catalyst of following general formula (I):

where:

X' is chosen from chloride, bromide, iodide or thiocyanate radicals or sulfonate radicals, advantageously perfluorinated on the carbon carrying the sulfonate functional group;

X is chosen from the values of X' and from radicals of formula Y-Z;

Y is chosen from the group of chalcogens, advantageously light chalcogens (that is to say, oxygen and sulfur);

Z is chosen from the group consisting of trisubstituted tin, monosubstituted zinc and residues of oxygen-comprising acids, the OH functional group not being included.

These isocyanates, masked in the form of carbonates, will be denoted in the continuation of the description under the term of carbamates.

These compositions, which can be used in the paint industry and more generally the coating industry, including adhesives, generally comprise, in addition, alcohols or apolyalcohols, or polyols which are described above.

These alcohol functional groups are advantageously primary alcohol functional groups.

This is because primary alcohols generally react more rapidly than secondary alcohols. The carbamates described above are advantageously carbamates of hydroxylated compounds chosen from alcohols which are volatile at a temperature at least equal to 150° C. and from hydroxylated masking agents. The hydroxylated masking agents, when they are not alcohols, even lato sensu, that is to say vinyl alcohols or phenols, are generally compounds comprising the —N—O—H bond. In other words, they are essentially compounds where the hydroxyl functional group is carried by the nitrogen. Mention may be made, among the families of these compounds, of hydroxyimides and oximes, in particular the oximes targeted by the European patent application (confers the application on behalf of the Applicant Company published under the number 0 869 982).

Oximes and hydroxyimides constitute a family of commonly used masking agents.

Another family of masking agents exhibiting a number of advantages is composed of phenols, advantageously exhibiting an electron-withdrawing functional group on the ring (see in particular the European patent application on behalf of the Applicant Company published under No. 0 680 984 and the international application published under No. 0 998 510).

When they are used as paint binder, the compositions comprise the usual additives for this use.

The present invention is also targeted at a transcarbamation process where use is made, as transcarbamation catalyst, of the compounds of formula (I):

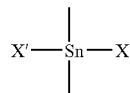

where:
X' is chosen from chloride, bromide, iodide or thiocyanate radicals or sulfonate radicals, advantageously perfluorinated on the carbon carrying the sulfonate functional group;
X is chosen from the values of X' and from radicals of formula Y-Z;
Y is chosen from the group of chalcogens, advantageously light chalcogens (that is to say, oxygen and sulfur);
Z is chosen from the group consisting of trisubstituted tin, monosubstituted zinc and residues of oxygen-comprising acids, the OH functional group not being included.

Advantageously, one of the X' or X groups is chosen from sulfonates perfluorinated on the carbon carrying the sulfonate functional group. These sulfonates advantageously correspond to the formula below:

EWG-(CX$_2$)$_p$— where:
the X groups, which are alike or different, represent a chlorine, a fluorine or a radical of formula $C_nF_{2n+1}$ with n an integer at most equal to 5, preferably to 2, with the condition that at least one of the X groups is fluorine, fluorine advantageously carried by the carbon connected to the sulfur;
p represents an integer at most equal to 2;
EWG represents an electron-withdrawing group (that is to say, $\sigma_p$ greater than zero, advantageously than 0.1, preferably than 0.2), the possible functional groups of which are inert under the conditions of the reaction, advantageously fluorine or a perfluorinated residue of formula $C_nF_{2n+1}$ with n an integer at most equal to 8, advantageously to 5, the total carbon number of Rf advantageously being between 1 and 15, preferably between 1 and 10.

Advantageously, X and X' are chosen from the compounds of above formula.

These catalysts make it possible to carry out the reaction at temperatures below 200° C., advantageously below 180° C.

Generally, in order to obtain satisfactory kinetics, it is advisable to be at a temperature at least equal to 100° C., preferably at a temperature at least equal to 120° C.

The following nonlimiting examples illustrate the invention. These examples, in order to avoid any interaction problems, related substantially to monofunctional isocyanates. n-Hexyl isocyanate was used.

EXAMPLE

General Procedure

Choice of the Reaction Model

The choice focused on the use of aliphatic isocyanates, which are more expensive but which give access to polyurethanes exhibiting:
better resistance to UV radiation,
a more stable color,
excellent behavior when used externally.

The action of primary alcohols gives carbamates which are very stable thermally in comparison with aromatic isocyanates.

Methanol was chosen as blocking agent for the alkyl isocyanate. This is because this alcohol is inexpensive, has a low molecular mass and has a limited toxicity.

A limitation on VOCs is promoted by such a blocking agent in comparison with the other agents. This methodology clearly falls within the scope of the development of a cleaner chemistry, an approach favored by current research.

Reactants Involved

The alkyl isocyanate chosen is hexyl isocyanate. It is blocked very simply with methanol with conventional heating for 4 hours. The reaction results in the formation of N-hexyl methyl urethane, which will be used as starting reactant during the transcarbamation reaction.

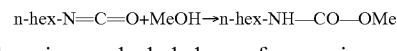

The primary alcohol chosen for carrying out the transcarbamation is octan-1-ol. The reaction of it with hexyl isocyanate with conventional heating for 4 hours results in the formation of the end product: N-hexyl octyl urethane.

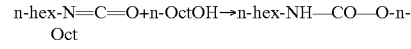

The characterization of this product by conventional analytical techniques was necessary in order to carry out kinetic monitoring of the transcarbamation reaction by gas chromatography (retention time and response factor).

Kinetic Study

The transcarbamation reaction studied, carried out in the absence of solvent and in the presence of 1 mol % of catalyst (in order to have a rapid reaction), is represented diagrammatically below:

$$\text{n-hex-NH—CO—OMe} + \text{OctOH} \xrightarrow{\text{Cat.}}$$
$$\text{carba 1}$$
$$\text{n-hex-NH—CO—Oct} + \text{MeOH}$$
$$\text{carba 2}$$

Carba 1: 3.14 mmol (500 mg)
OctOH: 1 eq. or 10 eq.
Internal reference (hexadecane): 0.5 eq.
Cat.: 1 mol %.
130° C.

Kinetic Results of Various Catalysts Tested

| Catalyst | k in mol$^{-1}$ · l · min$^{-1}$ | Yield (%) |
|---|---|---|
| Bu$_2$Sn(laurate)$_2$ reference | 1.10 · 10$^{-3}$ | 26 |
| Bu$_2$Sn(2-ethylhexanoate)$_2$ comparative | 7.32 · 10$^{-4}$ | 27 |
| BuSn(2-ethylhexanoate)$_3$ comparative | 3.34 · 10$^{-4}$ | 15 |
| Bu$_2$SnCl$_2$ | 9.73 · 10$^{-4}$ | 34 |
| Bu$_2$Sn(OMe)$_2$ comparative | 5.18 · 10$^{-4}$ | 17 |
| Bu$_2$SnCl(OAc) | 2.30 · 10$^{-3}$ | 53 |
| Bu$_2$SnBr(OAc) | 2.57 · 10$^{-3}$ | 55 |
| Bu$_2$Sn(NCS)$_2$ | 3.10 · 10$^{-3}$ | 63 |

As regards the control catalysts, such as dibutyltin diacetate and dibutyltin dilaurate, the latter display a very mediocre catalytic activity with yields at the end of the reaction of 43 and 26% respectively. Subsequently, a series of compounds comprising an alkanoate, halogen and methoxy ligand is observed, which compounds exhibit a relatively low effectiveness. The mixed halogen/acetate compounds show an excellent catalytic activity with good yields at the end of the reaction. However, these compounds are in fact mixtures between the tin(IV) compound and corresponding symmetrical and mixed distannoxanes. It will be seen below that the latter are very effective. Finally, dibutyltin diisothiocyanate proves to be the most active compound in this table with a rate constant of 3.10·10$^{-3}$ mol$^{-1}$·l.min$^{-1}$ and a final yield of 63%.

Catalysts Based on Distannoxanes

| Catalyst | k in mol$^{-1}$ · l · min$^{-1}$ | Yield (%) |
|---|---|---|
| [(AcO)Bu$_2$Sn]$_2$O | 1.39 · 10$^{-3}$ | 42 |
| [ClBu$_2$Sn]$_2$O | 1.84 · 10$^{-3}$ | 51 |
| [(NCS)Bu$_2$Sn]$_2$O | 3.54 · 10$^{-3}$ | 62 |
| [BrBu$_2$Sn]$_2$O | 5.10 · 10$^{-3}$ | 68 |
| [BrBu$_2$Sn]$_2$O (0.5 mol) | 2.93 · 10$^{-3}$ | 65 |
| [BrBu$_2$Sn]$_2$O (Amounts*10) | 2.48 · 10$^{-3}$ | 59 |
| (AcO)Bu$_2$Sn—O—Zn—OC$_5$H$_{11}$ | 1.12 · 10$^{-3}$ | 39 |

In the context of the transcarbamation reaction, compounds of this type also prove to be outstandingly effective. 1,3-Dibromotetrabutyldistannoxane proves to be the most effective here, with a rate constant of 5.10·10$^{-3}$ mol$^{-1}$·l.min$^{-1}$ and a final yield of 68%.

It should be noted that, even used at 0.5 mol % or with amounts of reactants 10 times greater, the results are still as good.

Nevertheless, it turns out that this type of compound results in the formation of a not insignificant amount of isocyanate in the reaction medium.

The invention claimed is:

1. A transcarbamation process, comprising the step of reacting a carbamate with an alcohol in the presence of an efficient catalytic amount, as transcarbamation catalyst, of compounds of general formula (I):

$$X'—\overset{|}{\underset{|}{Sn}}—X \qquad (I)$$

wherein:
   X' is chloride, bromide, iodide, thiocyanate radicals or sulfonate radicals;
   X is X' or radicals of formula Y-Z;
   Y is a chalcogen; and
   Z is trisubstituted tin, monosubstituted zinc or groups of oxygen-comprising acids, without the OH functional group.

2. The transcarbamation process according to claim 1, wherein:
   the X' sulfonate radicals are perfluorinated on the carbon carrying the sulfonate functional group; and
   Y is oxygen or sulfur.

3. The transcarbamation process according to claim 1, wherein the catalyst is used in an amount of at least equal to 0.5% and at most equal to 5% as carbamate functional group equivalent.

4. The transcarbamation process according to claim 3, wherein the amount is between 1% and 2%.

5. The transcarbamation process according to claim 1, wherein X is X'.

6. The transearbamation process according to claim 1, wherein one or more of the X or X' groups are halides or thiocyanates.

7. The transcarbamation process according to claim 1, wherein Z has the formula:

$$X'—\overset{|}{\underset{|}{Sn}}—X$$

wherein X' is as above defined.

8. The process according to claim 1, wherein the transcarbamation reaction is carried out at a temperature of between 100 and 200° C.

9. The process according to claim 8, wherein the temperature is between 120 and 180° C.

10. The process according to claim 1, wherein X' is a sulfonate radical perfluorinated on the carbon carrying the sulfonate functional group, and Y oxygen or sulfur.

11. A composition, comprising at least one carbamate capable of being obtained by reaction of a hydroxylated compound with an isocyanate and at least one compound of following general formula (I):

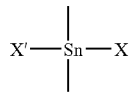 (I)

wherein:
X' are sulfonate radicals:
X is X' or radicals of formula Y-Z; and
Z is trisubstituted tin, monosubstituted zinc or groups of oxygen-comprising acids, without the OH functional group, wherein the isocyanate is aliphatic, the X' sulfonate radicals are perfluorinated on the carbon carrying the sulfonate functional group; and
Y is oxygen or sulfur.

12. The composition according to claim 11, further comprising an alcohol or polyalcohol.

13. The composition according to claim 12, wherein the alcohol or polyalcohol is primary.

14. The composition according to claim 12, wherein the hydroxylated compound is an alcohol volatile at a temperature at least equal to 150° C. or a hydroxylated masking agent.

15. The composition according to claim 14, wherein the masking agent is a phenol or an oxime.

16. The composition according to claim 12, wherein the hydroxylated compound is methanol.

17. The composition according to claim 11, wherein wherein X' is a sulfonate radical perfluorinated on the carbon carrying the sulfonate functional group, and Y oxygen or sulfur.

* * * * *